(12) United States Patent
Veldhuizen et al.

(10) Patent No.: US 7,625,377 B2
(45) Date of Patent: Dec. 1, 2009

(54) COLLAPSIBLE AND EXPANDABLE INSTRUMENT FOR INSERTION IN A DORSAL VERTEBRA

(75) Inventors: Albert Gerrit Veldhuizen, Eelde (NL); Kamiel Reiner Zale Geenen, Nederweert (NL)

(73) Assignee: Mandaco 569 Ltd (GB)

( * ) Notice: Subject to any disclaimer, the term of this patent is extended or adjusted under 35 U.S.C. 154(b) by 113 days.

(21) Appl. No.: 10/483,002

(22) PCT Filed: Jul. 1, 2002

(86) PCT No.: PCT/NL02/00429

§ 371 (c)(1),
(2), (4) Date: Dec. 31, 2003

(87) PCT Pub. No.: WO03/003951

PCT Pub. Date: Jan. 16, 2003

(65) Prior Publication Data

US 2005/0261683 A1    Nov. 24, 2005

(30) Foreign Application Priority Data

Jul. 2, 2001   (NL) .................................. 1018438

(51) Int. Cl.
*A61F 2/44* (2006.01)
*A61B 17/56* (2006.01)

(52) U.S. Cl. ................... 606/90; 606/105; 606/86 R; 606/99; 623/17.11

(58) Field of Classification Search ............ 606/86, 606/90, 105, 99, 205–208; 623/17.11–17.16; 600/222

See application file for complete search history.

(56) References Cited

U.S. PATENT DOCUMENTS

| | | | | |
|---|---|---|---|---|
| 3,677,129 A | * | 7/1972 | Lyon | 84/453 |
| 4,147,167 A | * | 4/1979 | Hickmann et al. | 606/107 |
| 4,898,161 A | * | 2/1990 | Grundei | 606/105 |
| 4,997,432 A | | 3/1991 | Keller | |
| 5,020,519 A | * | 6/1991 | Hayes et al. | 606/237 |
| 5,364,397 A | * | 11/1994 | Hayes et al. | 606/61 |
| 5,531,750 A | * | 7/1996 | Even-Esh | 606/79 |
| 5,782,832 A | | 7/1998 | Larsen et al. | |
| 6,039,761 A | * | 3/2000 | Li et al. | 623/17.16 |
| 6,127,597 A | | 10/2000 | Beyar et al. | |
| 6,174,334 B1 | | 1/2001 | Suddaby | |
| 6,224,604 B1 | * | 5/2001 | Suddaby | 606/80 |

(Continued)

FOREIGN PATENT DOCUMENTS

WO    WO 98/56301    12/1998

(Continued)

*Primary Examiner*—Eduardo C Robert
*Assistant Examiner*—Mary Hoffman
(74) *Attorney, Agent, or Firm*—Cantor Colburn LLP

(57) ABSTRACT

An instrument in particular suitable for being inserted into the cavity within a vertebra, which instrument features a collapsed position and an expanded position, in which collapsed position the instrument can be inserted into the cavity through an opening in the vertebral wall. The instrument includes a first upper elongated contact element and a second lower elongated contact element, and member for moving said elements apart in a direction substantially transversely to their contact surfaces to a particular end position, in which the elements are locked in position relative to each other.

24 Claims, 4 Drawing Sheets

U.S. PATENT DOCUMENTS

| | | | |
|---|---|---|---|
| 6,582,451 B1 * | 6/2003 | Marucci et al. | 606/207 |
| 6,620,196 B1 * | 9/2003 | Trieu | 623/17.16 |
| 6,814,737 B2 * | 11/2004 | Cauthen | 606/99 |
| 2002/0058947 A1 * | 5/2002 | Hochschuler et al. | 606/94 |
| 2003/0009169 A1 * | 1/2003 | Young et al. | 606/86 |
| 2003/0171812 A1 | 9/2003 | Grunberg et al. | |

FOREIGN PATENT DOCUMENTS

| | | |
|---|---|---|
| WO | WO 01/03616 A1 | 1/2001 |
| WO | WO 01/41652 | 6/2001 |

* cited by examiner

COLLAPSIBLE AND EXPANDABLE INSTRUMENT FOR INSERTION IN A DORSAL VERTEBRA

FIELD OF THE INVENTION

The present invention relates to an instrument in particular suitable for being inserted into the cavity within a vertebra, which instrument features a collapsed position and an expanded position, in which collapsed position the instrument can be inserted into the aforesaid cavity through an opening in the vertebral wall.

DESCRIPTION OF THE RELATED ART

If the quality of the bone tissue inside a vertebra deteriorates due to illness, such as osteoporosis, trauma and the like, the surrounding bone tissue may be subjected to an ever increasing pressure, which may lead to said tissue collapsing as well and the vertebra being compressed, with all the unpleasant consequences thereof.

Although various methods are known for restoring the height of an intervertebral disc; see International patent WO 01/03616, for example, only few suitable techniques are known for restoring the height of a damaged vertebra.

It is known, for example, to replace a damaged vertebra in its entirety by a prosthesis, but this is a very radical operation which is only performed in exceptional cases.

According to another, fairly recent technique for restoring damaged vertebrae, the vertebra is fixated with bone cement or the like. This method is disclosed in International patent application no. WO 98/56301. According to said method, the height of a crushed vertebra is restored by inserting an inflatable balloon into the cavity within the vertebra. The balloon is first inserted into said cavity in pressureless condition through a small opening in the vertebral wall, after which it is inflated, as a result of which the vertebra regains its original condition. Then the balloon is rendered pressureless again and removed, after which the space created inside the vertebra is filled with some kind of bone cement.

One drawback of this method is the fact that the inserted material is subjected to a pressure upon releasing of the balloon pressure, as a result of which said material may leak out, so that it will no longer perform its function to its full extent. Furthermore, the quality of the fusion between the inserted material and the surrounding bone tissue is not fully satisfactory, resulting in a less than optimum long-term strength and quality of the treated vertebra.

Nevertheless, in view of the rapid increase of the number of osteoporosis patients, there is a need for a relatively simple and reliable method for restoring damaged vertebrae. Consequently, it is an object of the present invention to provide an instrument by means of which a damaged vertebra can be restored in a relatively simple, i.e. with only relatively minor surgery being required, and qualitatively satisfactory manner.

SUMMARY OF THE INVENTION

An advantageous aspect of the invention is the fact that the instrument has been designed such that the surgeon can perform the operation with minimal invasive surgery. In order for the technique to become generally accepted, minor and rapid surgery and a short recovery time for the patient are essential.

Another advantageous aspect is the fact that the method employing the instrument according to the invention is quite similar to generally accepted techniques for restoring intervertebral discs, in particular to the so-called back approach. According to said approach, two blocks, also referred to as cages, are inserted into the intervertebral disc on either side of the spinal cord, restoring the spacing between the two adjacent vertebrae on either side and fixating the two vertebrae relative to each other. As is the case with the aforesaid conventional techniques for restoring intervertebral discs, the present instrument has two different functions, viz. restoration of the vertebra to its normal dimension and bearing the load on the vertebral body until sufficiently bone tissue has formed around the instrument that takes over the load. It must be possible for the surgeon to insert various kinds of material around the instrument, for example bone particles, minerals, etc, in order to accelerate bone growth without adversely affecting the bearing capacity of the instrument.

Another advantageous aspect is the fact that the restoration of the shape and the dimensions of the vertebral body can easily be checked by the surgeon, with the surgeon being able to withdraw the instrument if he is not absolutely certain that the instrument is correctly positioned.

The instrument according to the invention meets all the above requirements, and in order to achieve that, the instrument is characterized in that it comprises a first upper elongated contact element and a second lower elongated contact element, and in that means are present for moving said elements apart in a direction substantially transversely to their contact surface to a particular end position and fixating said contact elements relative to each other in said end position.

The instrument according to the invention may have a small width dimension and, in the collapsed position, also a small height dimension. In this position, the instrument can be inserted into the vertebral cavity via two small incisions in the patient's tissue and two small opening is in the vertebral wall. All this with a minimum degree of discomfort to the patient and under circumstances which ensure a quick recovery of the area in question. After the instrument has been inserted, the two contact elements are moved apart until they press against the upper and lower end faces of the vertebra in question with a specific, predetermined force in their end position, thus restoring the vertebra to its original dimension. In this position, the contact elements are fixated relative to each other. Now the surgeon can introduce a material, such as minerals or bone cement, into the space thus formed. The load on the vertebra is initially taken up nearly entirely by the instrument, so that bone growth can take place without the restored position of the vertebra being affected. Once a sufficient amount of bone of sufficient strength has been formed, said newly formed the bone will gradually take over the load on the instrument, all this analogously to the aforementioned cage techniques. Since the instrument has directly returned the vertebra to its original shape and fixated it therein, the pain which the patient experiences will be much less from the outset already.

It will be apparent that an instrument according to the invention is also very suitable for use as a vertebral prosthesis, in which a complete vertebra is replaced. Hereinafter a further explanation of the invention will be given by means of a description of the embodiment that is very suitable for use in a vertebra.

According to the invention, the means for moving the contact elements apart may be formed by all kinds of suitable mechanisms, for example hydraulic, pneumatic on mechanical mechanisms. Important is the fact is that all these mechanisms enable fixation of the elements relative to each other in their end position.

According to another embodiment of the instrument according to the invention, the means for moving the two contact elements apart are designed such that the position of one of the contact elements remains substantially unchanged during the aforesaid movement and that the movement is carried out by the other element.

According to another embodiment, it is the upper element whose position remains unchanged, in which case it is the lower contact element that moves towards the bottom of the vertebral cavity. The advantage of this embodiment is that a small access opening in the two bone structures practically at the ceiling of the vertebral cavity, also called pedicles, suffices to enable insertion of the instrument into the vertebral cavity. The instrument is introduced through said openings, and while the upper contact element remains in contact with the aforesaid ceiling, the lower contact element is moved downwards, i.e. away from the upper contact element, until it makes contact with the bottom, whereupon it is locked in position. All this will be explained in more detail yet hereinafter by means of an embodiment.

According to another advantageous embodiment, the lower contact element is pivotally connected to two parallel arms, which arms are also pivotally connected to a beam-shaped element at their upper sides, which beam-shaped element is slidably connected to the bottom side of the upper contact element.

According to another advantageous embodiment, a lever is pivotally connected to the upper contact element at one end and to one of the parallel arms at the other end, wherein the former pivot point is located approximately at the level of one parallel arm in the end position thereof and the latter pivot point is located between the ends of the second parallel arm.

The above embodiment comprises means for moving the beam-shaped element along the bottom side of the upper contact element. As a result of this movement, the parallelogram formed by the lower contact element and the two arms connected thereto will unfold and the lower contact element will move downwards in a direction away from the upper contact element.

According to another embodiment, the means for moving said beam-shaped element are formed by a cord or a cable, which is passed through an opening present in the upper contact element and whose ends are connected to tensioning means arranged on the beam-shaped element.

According to another embodiment, the aforesaid arms have a length such that the overall height dimension of the instrument in the expanded position thereof corresponds to the spacing between the bottom and the ceiling of the vertebral cavity. Said spacing must be measured for each case, which may be done by means of a measuring instrument of a construction similar to that of the instrument according to the invention, after which an instrument having the measured dimension must be inserted into the vertebral cavity.

The invention further relates to a method for using the instrument according to the invention. Said method is characterized in that two small openings are formed in the vertebral walls, through which openings the instrument is inserted in the collapsed position thereof, after which the instrument is expanded and locked in position in the vertebral cavity by suitable means.

According to another advantageous embodiment, said two small openings are formed in the upper part of the walls surrounding the vertebral cavity and the position of the upper contact element remains substantially unchanged upon expansion of the instrument, whilst the lower contact element is moved downwards in the direction of the bottom of the vertebral cavity.

After expansion and fixation of the two contact elements relative to each other, the vertebral cavity is according to the invention filled with a bone material or a mineral which stimulates the bone growth.

BRIEF DESCRIPTION OF THE DRAWINGS

The invention will be explained in more detail hereinafter by means of an embodiment.

DETAILED DESCRIPTION

Figure 2A:
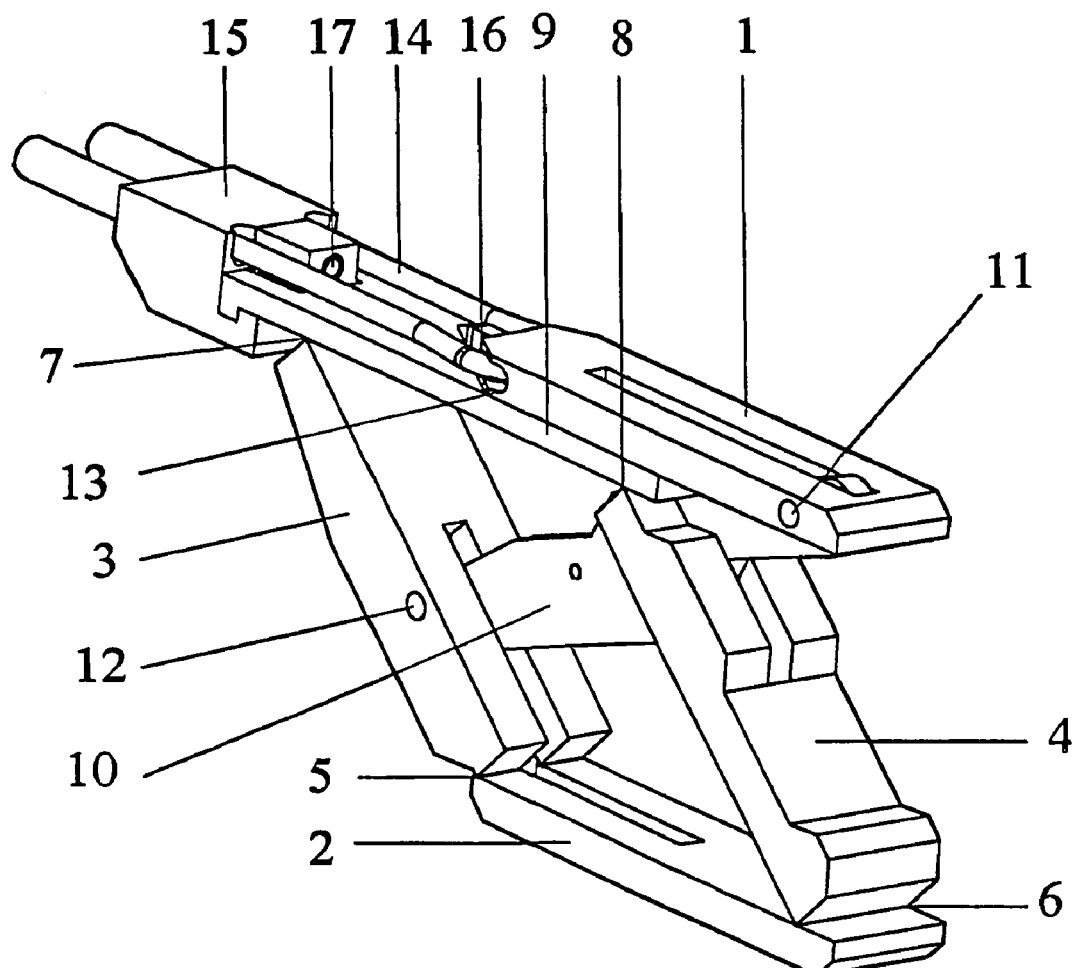
FIGS. 2a-b are perspective side elevations of the same instrument in a semi-expanded position (FIG. 2a) and a fully expanded and locked position (FIG. 2b).
Figure 2B:
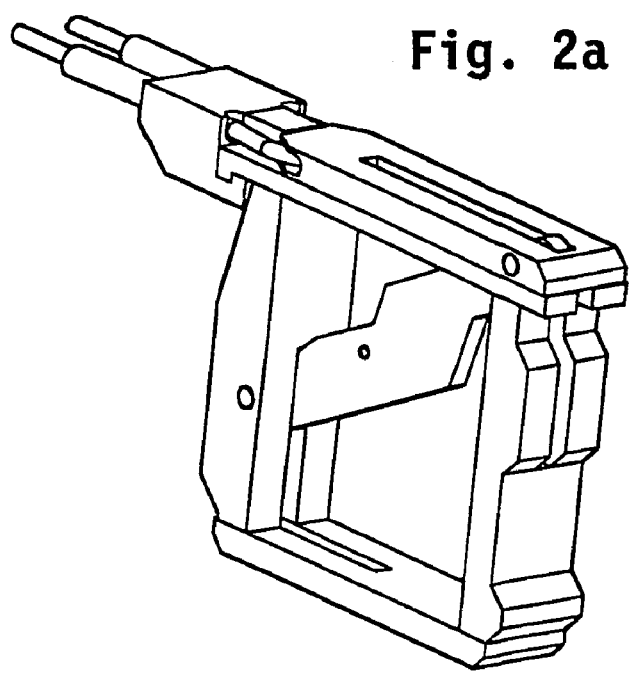

In FIG. 2a, numeral 1 indicates a first, upper, elongated contact element. Numeral 2 indicates a second, lower, likewise elongated contact element. Two parallel arms 3 and 4 are pivotally connected to the lower contact element 2 by means of hinges 5 and 6, respectively. At their other ends, the arms 3, 4 are pivotally connected, at points 7, 8, respectively, to a beam-shaped element 9 which is slidably connected to the bottom side of the upper contact element 1. In its end position as shown in FIG. 2b, a lever 10 is connected to the upper elongated contact element 1 with one end by means of a pivot 11, approximately at the level of parallel arm 4. The lever 10 is connected to the parallel arm 3, approximately at the centre thereof, with its other end by means of a pivot 12.

Figure 1A:
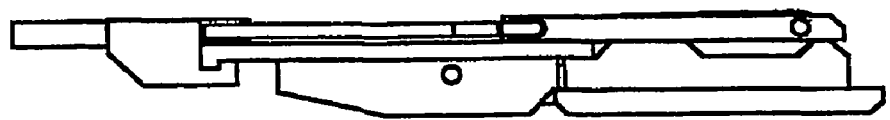
FIGS. 1a-d are side elevations of an embodiment of the instrument according to the invention, showing a number of operational positions ranging from a fully collapsed position (FIG. 1a) to a fully expanded and locked position (FIG. 1d).
Figure 1B:
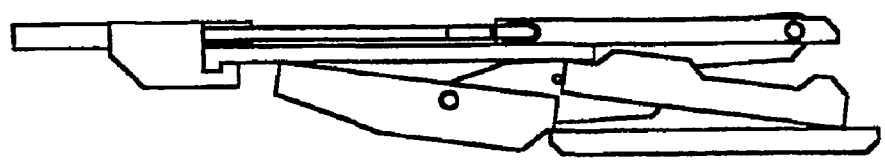
Figure 1C:
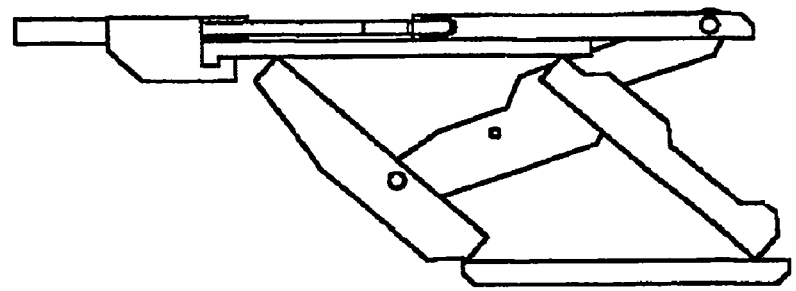
Figure 1D:
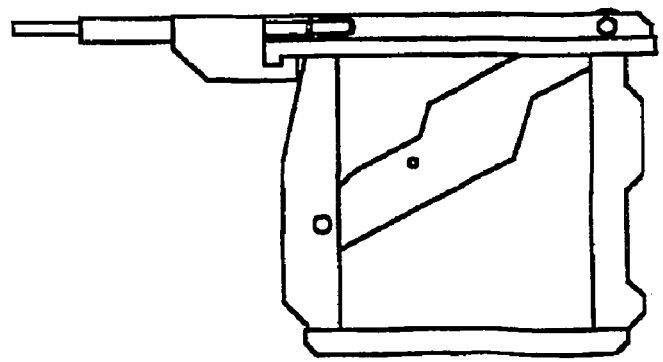

The upper contact element is provided with a cavity 13, through which a cord 14 is passed, the free ends of which are fixed in a detachable tensioning device 15 connected to the beam-shaped element 9, by means of which cord a pulling force can be exerted for the purpose of moving the instrument from its collapsed position as shown in FIG. 1a, via the intermediate stages as shown in FIGS. 1b-c, to its fully expanded position as shown in FIG. 1d. It should be noted in this connection that pulling of the cord 14 causes the beam-shaped element 9 to move to the right along the bottom side of the contact element 1, thus driving the lever 10, as a result of which the parallelogram formed by the lower element 2, the beam-shaped element 9 and the arms 3, 4 moves further and further towards its unfolded position. In FIG. 2, said parallelogram has reached its fully unfolded position, in which position it is locked as a result of the projecting part 16 on the upper contact element 1 mating with a cavity 17 in the beam-shaped element 9, such that the projecting part 16 is forced into the cavity 17, producing a friction between the two surfaces which causes the contact elements to be fixated relative to each other. It should be appreciated that elements 16 and 17 represent a fixator of the apparatus.

Figure 3A:
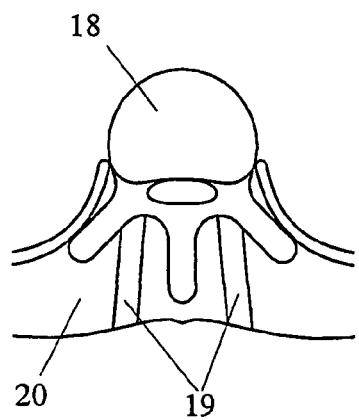
FIGS. 3a-c are various schematic, sectional representations of vertebrae and of the incisions and openings that must be formed so as to enable insertion of the instrument according to FIG. 1 into the vertebral body.
Figure 3B:
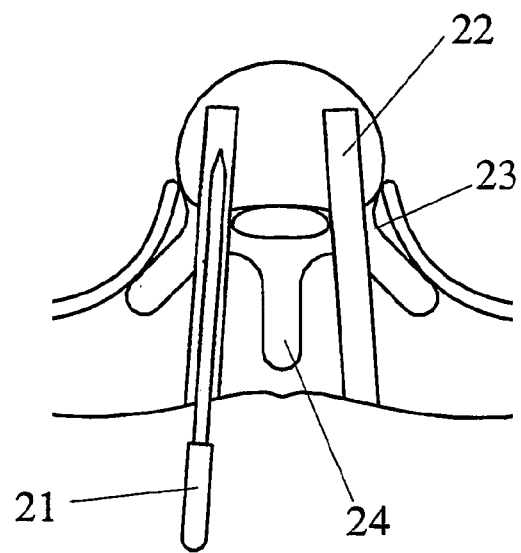
Figure 3C:
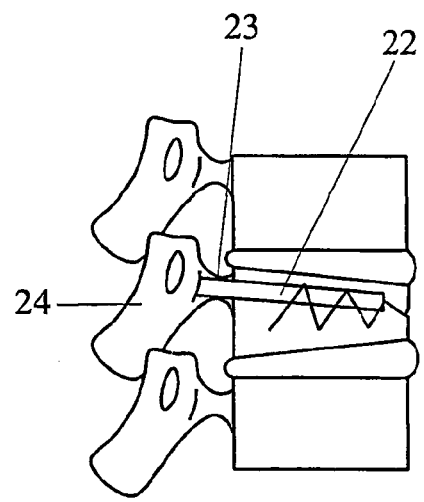

As is shown in FIGS. 3a-c, an instrument of the above-described kind can be introduced into a damaged vertebral body 18 by first making two fairly small incisions 19 in the tissue 20 of a patient. Following that, openings 22 are formed in said vertebral body by means of well-known and frequently used instruments 21, via the bone portion 23 which connects the rear part 24 of the vertebra to the vertebral body 18.

Figure 4A:
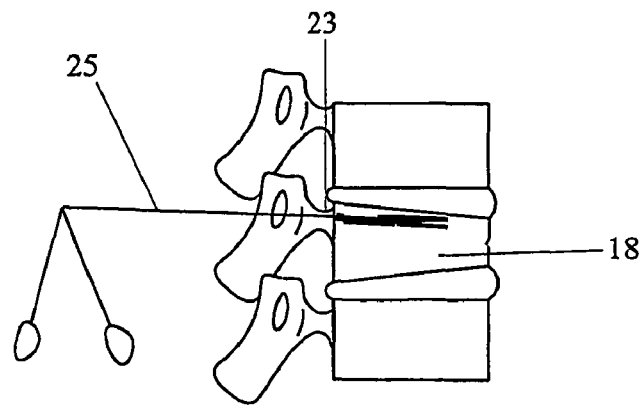
FIGS. 4a-c schematically show the various stages of the insertion of an instrument according to the invention into a vertebral body.
Figure 4B:
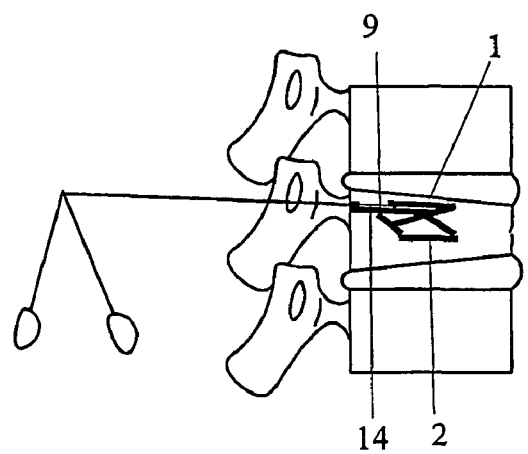
Figure 4C:
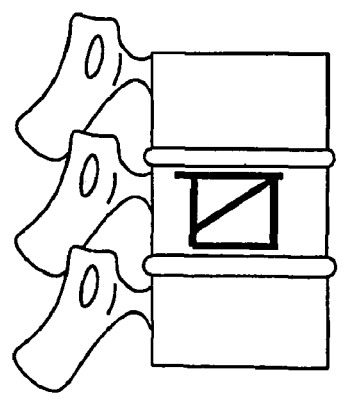

The insertion of the instrument is schematically shown in FIGS. 4a-c, which clearly show that in a first stage, as shown in FIG. 4a, the instrument is pushed into the bone portion 23 through the aforesaid openings (not shown) in its collapsed position by means of an auxiliary insertion element 25 and placed into the vertebral cavity 18. It is noted that the aforesaid openings are located so high that the first upper contact element 1 practically abuts against the ceiling of the vertebral cavity. Subsequently, the instrument is expanded by moving the beam-shaped element 9 to a position under the contact element 1 by means of the auxiliary element 25, using the cord 14, upon which movement the lower contact element 2 moves downwards in the direction of the bottom of the vertebral cavity. FIG. 4c shows the stage where said expansion is complete and the instrument is fixated. In addition, the auxiliary element 25 is disconnected from the instrument. If the surgeon should decide just before the fixation stage that the instrument is not correctly positioned in the vertebral cavity, he will be able to collapse the instrument again and withdraw it through the aforesaid openings.

The expanding instrument has stretched the vertebra substantially to its original dimension, as it were. The instrument can now take up loads that are exerted on the vertebra. The space that has been formed within the vertebra can now be filled with a mineral material or another material which stimulates the bone growth. Since the instrument takes up any loads that are exerted on the vertebra, bone growth can take place without any risk of forces being exerted on the vertebra causing the bone that has grown to collapse again, thus forcing out the inserted material. This leads to a satisfactory restoration procedure for a damaged vertebra, which can be realised by means of an instrument of simple design and a relatively simple surgical procedure.

The invention claimed is:

1. A method for restoring a collapsed or damaged vertebral cavity, comprising:
    forming an opening into an interior region of said vertebral cavity;
    selecting an implantable device and attaching said implantable device to an auxiliary insertion element, wherein the implantable device is selected to comprise a first upper elongated contact element having a first contact surface; a beam element slidably connected to a bottom side of the upper contact element; a second lower elongated contact element having a second contact surface; parallel arms pivotally connected at upper ends to said beam shaped element and at lower ends to said lower contact element; and a mover configured to move said elements apart in a direction substantially transversely to their contact surfaces to an expanded position so as to open a space between said upper and lower contact elements;
    inserting said implantable device to distance bones of said vertebral cavity from each other, thereby forming a space within said interior region of said vertebral cavity;
    expanding said implantable device to restore said vertebral cavity to a substantially restored condition, thereby forming a space within said interior region of said vertebral cavity;
    fixating said implantable device to provide a structure that supports said vertebral cavity; and
    detaching said implantable device from said auxiliary insertion element so as to leave the implantable device within said interior region.

2. A method as claimed in claim 1, wherein said implantable device is expanded so as to restore said vertebral cavity to a substantially restored condition.

3. A method as claimed in claim 1, wherein said opening comprises two small openings in the walls surrounding a vertebral cavity and the upper contact element abuts against the ceiling of said cavity upon expansion of the instrument, as a result of which its position remains substantially unchanged, whilst said expansion substantially takes place by moving the lower contact element downwards.

4. A method as claimed in claim 1, wherein after expansion and fixation of the two contact elements in their end position relative to each other, the vertebral cavity is filled with a repairing material.

5. A method as claimed in claim 1, wherein after expansion and fixation of the two contact elements in their end position relative to each other, the vertebral cavity is filled with a material selected from a list comprising: a bone material; a mineral material or another material which stimulates bone growth.

6. A method for restoring a collapsed or damaged vertebral cavity, comprising the steps of:
    forming an opening into an interior region of said vertebral cavity;
    selecting a device comprising: a first upper elongated contact element having a first contact surface; a beam element slidably connected to a bottom side of the upper contact element; a second lower elongated contact element having a second contact surface; parallel arms pivotally connected at upper ends to said beam shaped element and at lower ends to said lower contact element; and a mover configured to move said beam element slidably along the lower surface of said upper contact element and said lower contact element away from said upper contact element in a direction substantially transverse to said upper contact element, whilst maintaining a position of the upper contact element;
    inserting said device into said interior region;
    expanding said device to, distance bones of said vertebral cavity from each other and thereby form a space within said interior region of said vertebral cavity; and
    filling the vertebral cavity with a repairing material.

7. A method as claimed in claim 6, wherein said repair material is selected from a list comprising: a bone material; a mineral material or another material which stimulates bone growth.

8. A method as claimed in claim 6, including the further step of removing said device from said vertebral cavity.

9. A method as claimed in claim 6, wherein said opening comprises two small openings in the walls surrounding a vertebral cavity and the upper contact element abuts against the ceiling of said cavity upon expansion of the instrument, as a result of which its position remains substantially unchanged, whilst said expansion substantially takes place by moving the lower contact element downwards.

10. A method as claimed in claim 6, wherein after expansion and fixation of the two contact elements in their end position relative to each other, the vertebral cavity is filled with a material selected from a list comprising: a bone material; a mineral material or another material which stimulates bone growth.

11. An instrument for expanding a vertebral cavity, which instrument features a collapsed position and an expanded position wherein said instrument comprises:
    a first upper elongated contact element having a first contact surface;

a beam element in contact with and connected to a bottom side of the upper contact element;

a second lower elongated contact element having a second contact surface;

parallel arms pivotally connected at upper ends to said beam shaped element and at lower ends to said lower contact element;

a mover configured to move said beam element slidably along the lower surface of said upper contact element and said lower contact element away from said upper contact element in a direction substantially transverse to said upper contact element, whilst maintaining a position of the upper contact element; and a lever pivotally connected to said beam element at one end and pivotally connected at a point between the ends of a parallel arm at the other end.

12. An instrument as claimed in claim 11 and further comprising a fixator configured to fix said contact elements relative to each other in said expanded position.

13. An instrument according to claim 11, wherein the mover is a hydraulic device.

14. An instrument according to claim 11, wherein the mover is pneumatic device.

15. An instrument according to claim 11, wherein the mover is a mechanical device.

16. An instrument according to claim 11, wherein one of said parallel arms is slidably connected to said beam element.

17. An instrument according to claim 11 one of said parallel arms is slidably connected to said beam element and the position of the upper element remains unchanged during the aforesaid movement and wherein the lower element moves away from the upper element.

18. An instrument according to claim 11 wherein the two parallel arms are connected to the lower contact element via hinges.

19. An instrument according to claim 11 and including a tensioning device for moving the beam element along the bottom side of the upper contact element, thereby to cause said lower contact surface to move between respective positions.

20. An instrument according to claim 11 and including a tensioning device configured to move the beam element along the bottom side of the upper contact element, thereby to cause said lower contact surface to move between respective positions and wherein the upper contact element includes an opening and the tensioning device comprise a cord or a cable, which is passed through said opening and whose ends are connected to tensioning device arranged on the beam element.

21. An instrument according to claim 11, wherein said arms have a length such that the overall height dimension of the instrument in the expanded position thereof corresponds to the spacing between the bottom and the ceiling of a vertebral cavity.

22. An instrument according to claim 11, and including a fixator configured to fix the contact elements in their end position, said fixator being disposed on the upper contact element and on the beam element.

23. An instrument according to claim 22, wherein the upper contact element includes a projecting part and the beam-shaped element includes a cavity, wherein the projecting part of the upper contact element mates with the cavity in the beam element in such a manner that a friction between the two surfaces is produced in the end position, which friction cause the contact elements to be fixated relative to each other.

24. An instrument as claimed in claim 11 wherein said instrument comprises a vertebral prosthesis.

* * * * *